(12) United States Patent
Calasso

(10) Patent No.: US 10,413,657 B2
(45) Date of Patent: Sep. 17, 2019

(54) MEDICAMENT INFUSION DEVICE

(71) Applicant: Medirio S.A., Visp (CH)

(72) Inventor: Irio Giuseppe Calasso, Arth (CH)

(73) Assignee: Medirio S.A., Visp (CH)

(*) Notice: Subject to any disclaimer, the term of this patent is extended or adjusted under 35 U.S.C. 154(b) by 0 days.

(21) Appl. No.: 13/910,698

(22) Filed: Jun. 5, 2013

(65) Prior Publication Data

US 2013/0338592 A1   Dec. 19, 2013

(30) Foreign Application Priority Data

Jun. 14, 2012  (EP) .................................. 12172092

(51) Int. Cl.
   *A61M 5/14*        (2006.01)
   *A61M 5/142*       (2006.01)

(52) U.S. Cl.
   CPC .... *A61M 5/14248* (2013.01); *A61M 5/14232* (2013.01); *A61M 2005/1402* (2013.01);
   (Continued)

(58) Field of Classification Search
   CPC .......... A61M 5/14248; A61M 5/14232; A61M 2005/14268; A61M 2205/6054;
   (Continued)

(56) References Cited

U.S. PATENT DOCUMENTS 5,843,037 A * 12/1998 Uber, III ........... A61M 5/16827
                                                604/151
6,358,239 B1 * 3/2002 Rake ..................... A61M 5/148
                                                128/DIG. 12
(Continued)

FOREIGN PATENT DOCUMENTS

WO   WO 2010/072005 A1   9/2009
WO   WO 2009/113075 A1   7/2010

OTHER PUBLICATIONS

Merriam-Webster Dictionary definition of assembled, available online Apr. 22, 2017 at https://www.merriam-webster.com/dictionary/assembled.*

*Primary Examiner* — Amber R Stiles
(74) *Attorney, Agent, or Firm* — Blank Rome LLP

(57) ABSTRACT

The present invention refers to a medical device for transdermal infusion of a medicament comprising a reservoir for holding a medicament to be infused, a pump for pumping medicament from the reservoir, wherein the device is assembled or adapted to be assembled in at least one pre-operational arrangement with or without the reservoir and is adapted to be rearranged from the at least one pre-operational arrangement into an operational arrangement comprising the reservoir. In particular, in the pre-operational arrangement without reservoir the pump is in a mechanically distressed condition preventing functional operation of the pump, and in the pre-operational arrangement comprising the reservoir the pump is in a mechanically distressed condition preventing functional operation of the pump and/or the reservoir is fluidically disconnected from the pump. In the operational arrangement the pump is in a mechanically stressed condition enabling functional operation of the pump and the reservoir is fluidically connected to the pump.

13 Claims, 10 Drawing Sheets

(52) U.S. Cl.
CPC .............. *A61M 2005/14252* (2013.01); *A61M 2005/14268* (2013.01); *A61M 2205/6054* (2013.01); *A61M 2205/8287* (2013.01)

(58) Field of Classification Search
CPC ........... A61M 2005/14252; A61M 2205/8287; A61M 2005/1402
USPC ....... 604/131, 151, 174, 180–181, 186, 197, 604/246, 256, 257, 259, 890.1
See application file for complete search history.

(56) References Cited

U.S. PATENT DOCUMENTS

| | | | | |
|---|---|---|---|---|
| 6,595,956 | B1* | 7/2003 | Gross | A61M 5/14248 128/DIG. 12 |
| 6,702,779 | B2* | 3/2004 | Connelly | A61M 5/14248 604/890.1 |
| 7,637,891 | B2* | 12/2009 | Wall | A61K 9/0019 604/131 |
| 2002/0077601 | A1* | 6/2002 | Kawagishi | A61M 5/20 604/224 |
| 2002/0151846 | A1* | 10/2002 | Christenson | A61M 5/14232 604/131 |
| 2002/0169439 | A1* | 11/2002 | Flaherty | A61M 5/14248 604/891.1 |
| 2002/0172615 | A1* | 11/2002 | Woodworth | A61L 2/087 422/22 |
| 2003/0073952 | A1 | 4/2003 | Flaherty et al. | |
| 2003/0216684 | A1* | 11/2003 | Fentress | A61M 5/145 604/81 |
| 2007/0106218 | A1* | 5/2007 | Yodfat | A61M 5/1413 604/131 |
| 2008/0255516 | A1* | 10/2008 | Yodfat | A61M 5/14248 604/151 |
| 2008/0319414 | A1* | 12/2008 | Yodfat | A61B 5/6849 604/506 |
| 2009/0118676 | A1* | 5/2009 | Emmott | A61M 5/002 604/195 |
| 2010/0004596 | A1* | 1/2010 | De Polo | A61M 5/1413 604/131 |
| 2010/0121306 | A1* | 5/2010 | Yodfat | A61M 5/14532 604/500 |
| 2010/0130931 | A1* | 5/2010 | Yodfat | A61M 5/14248 604/151 |
| 2010/0204657 | A1* | 8/2010 | Yodfat | A61M 5/14248 604/181 |
| 2011/0144587 | A1 | 6/2011 | Stone | |
| 2012/0078170 | A1* | 3/2012 | Smith | A61M 5/14216 604/67 |

* cited by examiner

MEDICAMENT INFUSION DEVICE

FIELD OF THE INVENTION

The present invention relates to a device for the trans-dermal infusion of medicament. The invention also refers to a kit for assembling such a device and to a method of manufacturing such device.

BACKGROUND OF THE INVENTION

Many medical conditions often require the regular infusion of doses of medicaments as medical treatment. These medicaments are often provided as liquid solutions to be trans-dermally infused. Diabetic patients, for example, may require several infusions of insulin every day. Patients with chronic diseases may require frequent doses of a pain drug, etc. . . . Mostly, these patients use infusion pen devices, because they allow an easier and more convenient administration of doses of medicament than with standard syringe and vial. Pen devices however still require complex manipulations, like assembling a new needle every time, replacing a medicament vial when empty, and force the patient to make a new injection every time. This may cause various problems like possible contamination, uncomfortable and embarrassing situation in public place, sore body parts due to multiple infusion points. In the attempt to make the life of these patients easier, infusion devices have been developed. The infusion devices known in the art typically comprise a syringe, and use electro-mechanical pumping to deliver the medicament to the patient via tubing through the skin. They typically comprise also all the elements needed for operation and control, e.g. a processor, electric components, a battery, buttons or switches located on the housing of the device, visual feedback via text or graphic screen, such as an LCD, etc. . . . Currently available infusion devices are expensive, difficult to use and tend to be bulky and uncomfortable. Moreover, they require specialized care, maintenance and cleaning to assure proper functionality and safety for their intended long-term use.

It is thus preferable to use medical infusion devices such as that disclosed in US2012245515A1, incorporated herein by reference, which comprise a minimum number of components, are therefore small and cheap and may be disposable. Moreover, such devices are comfortable, discreet and easy to use. In addition, they are safe to use since they can be activated and controlled in a specific manner via a separate hand-held device, wherein the hand-held device is also the energy source for the infusion device. The hand-held device therefore provides the infusion device from the outside with the energy and control required for pumping a dose of medicament.

SUMMARY OF THE INVENTION

It is against the above background that the present invention provides certain unobvious advantages and advancements over the prior art. In particular, a new device for trans-dermal infusion of a medicament is described, which is even safer and more reliable to use.

The medical device comprises a reservoir for holding a medicament to be infused, a pump for pumping medicament from the reservoir, wherein the device is assembled or adapted to be assembled in at least one pre-operational arrangement with or without the reservoir and is adapted to be rearranged from the at least one pre-operational arrangement into an operational arrangement comprising the reservoir. In particular, in the pre-operational arrangement without reservoir the pump is in a mechanically distressed condition preventing functional operation of the pump, and in the pre-operational arrangement comprising the reservoir the pump is in a mechanically distressed condition preventing functional operation of the pump and/or the reservoir is fluidically disconnected from the pump. In the operational arrangement the pump is in a mechanically stressed condition enabling functional operation of the pump and the reservoir is fluidically connected to the pump.

Thus the device is displaceable from at least one pre-operational arrangement to an operational arrangement. In particular, the device is assembled or adapted to be assembled in a pre-operational arrangement, in which the device component or components most susceptible to mechanical stress when the device is in operation are in a mechanical distressed condition, and the end user, i.e. the patient or a care giver, is supposed to switch from the pre-operational arrangement to the operational arrangement in order to be able to use the device. An advantage of this is that the shelf life and also the reliability of the device during use can be increased. This enables also to pre-load the device with the medicament during manufacture, which makes the device particularly easy and convenient to use. In addition or in alternative, in case the device is pre-loaded with the medicament, the medicament may be isolated in a reservoir in the pre-operational arrangement and become fluidically connected with a pump in the operational arrangement. This also contributes to increase the shelf life and the reliability of the device, since the medicament may be better sealed from the external environment and prevented to come in contact with other parts of the device, which may be less suitable than the reservoir for long storage of the medicament. The displaceable arrangement of the device components may be also used to enable easy introduction of the medicament into the device and to prevent further introduction after the first use, thus preventing misuse. In particular, the device may be adapted such that introduction of the medicament can occur only in a pre-operational arrangement and use for medical infusion can occur only in the operational arrangement.

The present invention refers also to kit, e.g. a ready to assemble kit, comprising a plurality of components adapted to be assembled together such as to form the device in a pre-operational arrangement.

The present invention refers also to a method of manufacturing device components adapted to be assembled in a pre-operational arrangement.

These and other features and advantages will be more fully understood from the following detailed description taken together with the accompanying claims. It is noted that the scope of the claims is defined by the recitations therein and not by the specific discussion of features and advantages set forth in the description.

BRIEF DESCRIPTION OF THE DRAWINGS

The following detailed description can be best understood when read in conjunction with the following drawings, where like structure is indicated with like reference numerals and in which.

DETAILED DESCRIPTION

Figures 1A, 1B:
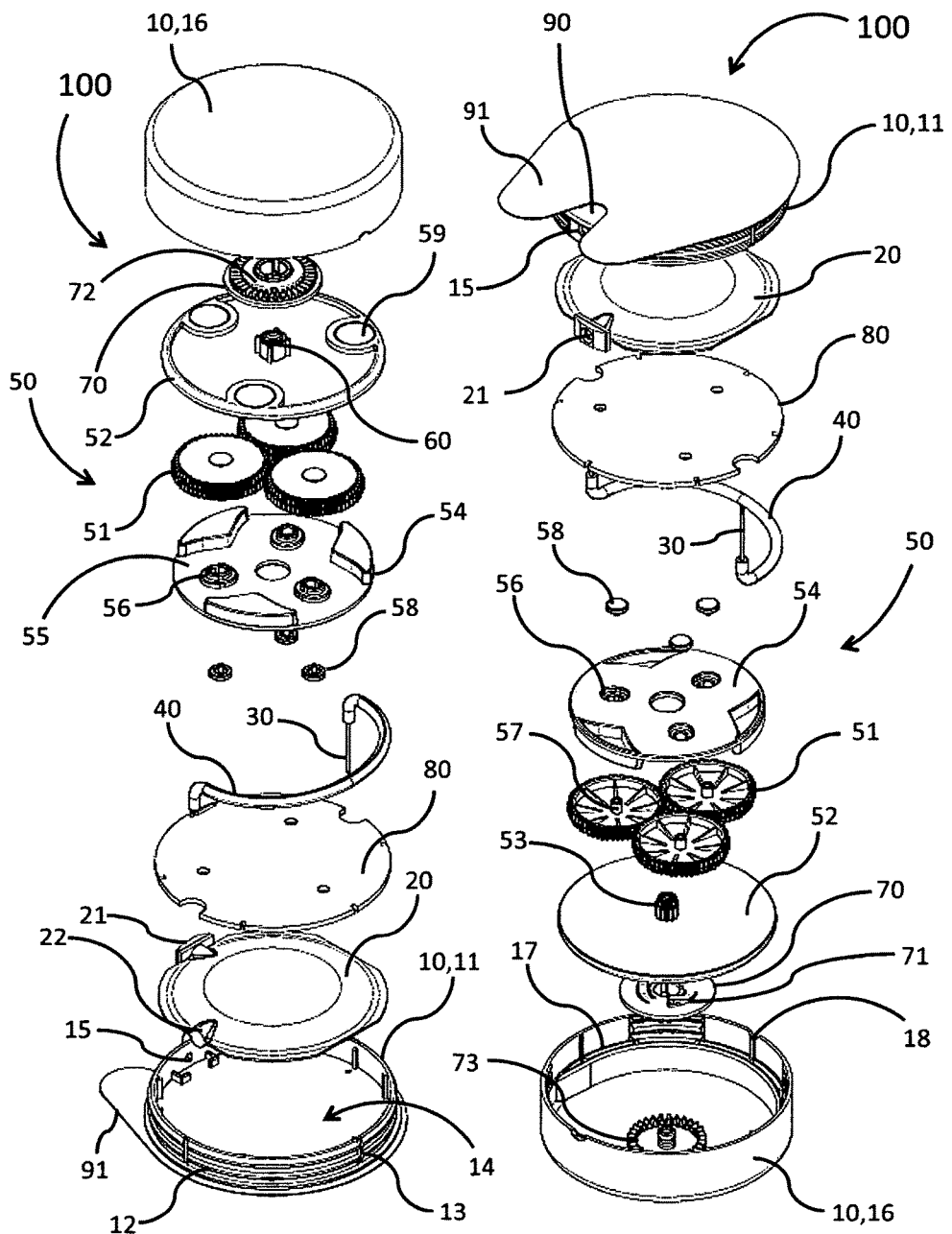
FIG. 1a and FIG. 1b are exploded views of a medical device for trans-dermal infusion of a medicament wherein the device components are seen from different perspectives respectively.

"Trans-dermal infusion" is herein used to indicate that the medical device is adapted to deliver trans-dermally, i.e. through the skin, a medicament to a patient without the need of multiple injections. The term "trans dermal infusion" thus comprises analogous terms such as intra-muscular, intra-venous, etc. . . . as far as infusion occurs via penetration of the skin.

A "medical device" is thus a device, which is adapted to be in body contact with a patient at least via an infusion element and to perform medical treatment by infusing e.g. a dose of medicament to the patient when requested. The medical device may otherwise be adapted as a continuous delivery device, to infuse a continuous flow of a medicament over a prolonged period of time, wherein the flow rate may be adjusted. For convenience, the device may be adapted to be removably fixed, e.g. with an adhesive layer or base to the skin of the patient. A typical example of patient is a diabetic patient requiring frequent doses of insulin, e.g. in correspondence to each meal. The device may be provided with an internal energy source or it may be an energy-passive device adapted to receive energy from an external hand-held device, e.g. inductively, e.g. by electromagnetic coupling, to pump the requested dose of medicament.

The medical device comprises a reservoir for holding a volume of a medicament to be delivered which is sufficient for several doses. The medical device can be disposable and thus intended to be replaced after a period of time, e.g. 1 to 7 days, typically 2 to 4 days, after several doses of the medicament have been infused, e.g. when the medicament is exhausted or the reservoir is nearly empty. The reservoir may be any type of container with any shape, suitable to contain a medicament of choice. The reservoir thus comprises a chemical- and/or bio-compatible material inert to the medicament to be contained. According to certain embodiments the reservoir is pre-loaded with the medicament in the manufacturing process. The reservoir may thus be suitable for storing a medicament within the device for a long period of time, e.g. several months or years before the device is used. According to certain embodiments the reservoir is adapted to be loaded with the medicament by the user, i.e. the patient or care giver, before use. According to certain embodiments the reservoir is adapted to be loaded in the device before use, either before or after loading the reservoir with the medicament. The term "in or into the device" is herein used to indicate any position with respect to the device, e.g. inside the device or attached to the device such as to become a functional unit of the device.

According to certain embodiments the reservoir is a collapsible pouch, adapted to expand from a collapsed status to an expanded status upon loading the reservoir with the medicament and from an expanded status to a collapsed status upon emptying the reservoir, e.g. upon pumping the medicament.

The medical device may comprise an infusion element or may be adapted to be fluidically connected to an infusion element. The infusion element is adapted for the trans-dermal infusion of the medicament, i.e. adapted to remain in a trans-dermal position for the duration of use of the medical device such as to allow infusion a dose of medicament from the medical device into the body when requested. The infusion element may comprise a thin needle insertable at a controlled depth, a cannula, a catheter, or other form of hollow fluid transport conduit, insertable e.g. via a removable needle, and adapted to infuse a medicament. The infusion element may comprise or be made of metal such as steel, of a ceramic material, of a silica-based material, of a polymeric material such as silicone or Teflon, or any composite thereof. The infusion element may comprise one or more outlets, e.g. a plurality of micro-needles, adapted to penetrate the skin and/or infuse the medicament in parallel or sequentially. The infusion element may comprise a triggering element, comprising e.g. a resilient element, e.g. a spring, adapted to trigger skin penetration to a controlled depth.

The medical device comprises a pump for pumping the medicament from the reservoir, e.g. from the reservoir to the infusion element and thus through the infusion element to the patient.

The medical device is assembled or adapted to be assembled in at least one pre-operational arrangement and is adapted to be rearranged from the at least one pre-operational arrangement into an operational arrangement.

A "pre-operational arrangement" is a three-dimensional space arrangement of the device components, wherein use of the device for medical treatment is disabled. In other words proper operation of the device is impeded, e.g. by preventing proper operation of the pump and/or by interrupting the fluid connection between the reservoir and the pump, and/or by being unresponsive to any control or command intended to operate the device. A pre-operational arrangement may or may not comprise the reservoir.

An "operational arrangement" is a three-dimensional arrangement of the device components, wherein use of the device for medical treatment is enabled, i.e. the device is capable of proper operation under controlled conditions, for a certain period of time, e.g. at the latest until the medicament in the device is exhausted. "Proper operation" means that the device is responsive to a specific command or control intended to operate the device for medical treatment, and is capable of executing the command as expected, e.g. to use energy received from an external hand-held device to pump the requested dose of medicament. The operational arrangement thus comprises all components needed for proper operation, including the reservoir, and all components are in an operational condition. Loading of the reservoir in the device may be part of the rearrangement from a pre-operational arrangement without reservoir into the operational arrangement with the reservoir. The infusion element may be fluidically connected after the rearrangement from the at least one pre-operational arrangement into the operational arrangement.

The rearrangement from a pre-operational arrangement into the operational arrangement is necessary in order for the device to become operational, i.e. capable of proper operation. In practice, this can be achieved e.g. by biasing two or more elements of the device with respect to each other. For example, the device may comprise a housing, wherein the housing may comprise two parts, e.g. a base and a cover, which are adapted to be biased with respect to each other, e.g. adapted to be pushed against each other and/or to be pulled apart from each other until a stop position is reached and/or to be at least in part rotated with respect to each other.

This movement causes the internal rearrangement of that or those components of the device, which are in a pre-operational condition into a respective operational condition. The biasable elements may be adapted to return to the original position or to an intermediate position after triggering an irreversible rearrangement of that or those components, which are in a pre-operational condition into a respective operational condition. The device may comprise a movable element, such as a pin, tongue or the like adapted to be moved with respect to the housing, e.g. inserted or removed or displaced, thereby causing the necessary rearrangement. The device may be adapted such as the rearrangement may be carried out manually, automatically or semi-automatically, e.g. via one or more motors or triggering element internal to the device.

There may be different pre-operational arrangements, e.g. at different stages of the device lifetime from manufacturing to use, e.g. intermediate pre-operational arrangements, in which different or additional pre-operational conditions are met or new operational conditions are added as needed. There is however only one operational arrangement enabling proper operation for medical infusion. In particular, in the at least one pre-operational arrangement at least one operational condition is unmet, whereas in the operational arrangement all operational conditions are met.

In particular, there may be a pre-operational arrangement without reservoir wherein the pump is in a mechanically distressed condition preventing functional operation of the pump. There may be a pre-operational arrangement comprising the reservoir wherein the pump is in a mechanically distressed condition preventing functional operation of the pump and/or the reservoir is fluidically disconnected from the pump.

Whereas in the operational arrangement the pump is in a mechanically stressed condition enabling functional operation of the pump and the reservoir is fluidically connected to the pump.

The pump may be any sort of pumping mechanism, e.g. a peristaltic pump, a membrane pump, an electro-osmotic pump, a micropump, as known in the art, located between the reservoir and the infusion element and adapted for pumping the medicament from the reservoir towards the infusion element.

According to certain embodiments, the device comprises a tubing for transporting medicament from the reservoir to the infusion element. The term "tubing" refers in general to any hollow fluid transport conduit for transporting medicament from the reservoir to the infusion element. It may be made of metal or polymer or composite material, made of one piece or more pieces directly or indirectly connected to each other, e.g. via a tubing connector and/or via a pump and/or via a chamber. The tubing is not limited to any particular geometry or form and may comprise parts having different cross-sections, such as e.g. a part with a tubular or cylindrical cross-section and a part such as a chamber with a substantially rectangular cross-section. The term "tubing" thus refers to any type of fluid conduit internal to the housing of the device whereas the term "infusion element" refers to a conduit at least in part external to the housing of the device. The infusion element may be fluidically connected or connectable to the tubing either inside or outside of the housing of the device. The infusion element may be however embodied as an extension of the tubing, characterized as infusion element only by its terminal location outside of the housing of the device.

According to certain embodiments, the pump comprises the tubing. In other words, the tubing is part of the pumping mechanism and cooperates to pump the medicament when the pump is in operation, e.g. by peristaltic pumping. The tubing is therefore in such a case one component of the device, which is susceptible to mechanical stress. According to certain embodiments, in the at least one pre-operational arrangement the tubing is mechanically distressed and in the operational arrangement the tubing is mechanically stressed, such as to enable operation of the pump.

The term "mechanical stress" or "mechanically stressed" is herein used with respect to a component of the device to indicate that a force is applied to that component or at least to part of that component, e.g. to one or more segments, areas or surfaces, or points, by another one or more components, wherein such a force, if prolonged over time, may cause deformation and/or weakening and/or loss of elasticity and/or loss of other operational characteristic of the component susceptible to mechanical stress, which may compromise proper operation. Mechanical stress does not necessarily need to occur during the rearrangement from a pre-operational arrangement to the operational arrangement. According to certain embodiments mechanical stress may be applied after the rearrangement into the operational arrangement, e.g. when operation of the device is initiated. For example, the tubing may be mechanically stressed when the pump starts to operate in the operational arrangement. This could be achieved for example with an ex-centric peristaltic wheel. The term "mechanically stressed" therefore includes the term mechanically stressable in the operational arrangement.

The term "mechanically distressed" is herein used with respect to a component of the device to indicate that no force or less force, compared to a mechanically stressed component, is applied to at least a part or parts of that component playing an important role for proper operation of the device. Force may however be applied to other parts playing a less important or no role for proper operation of the device. For example, the tubing may be occluded by pressure upstream or downstream of the pump, e.g. to close the fluidic connection with the reservoir.

With particular reference to the pump, the pump may be in a mechanically distressed pre-operational condition if the tubing, or at least the segment or segments of the tubing cooperating with the pumping mechanism in operation, is mechanically distressed and/or if other pump components susceptible to mechanical stress in operation such as e.g. gear components, valve components, piston or the like components, O-ring or other sealing components, etc. . . . are mechanically distressed.

According to certain embodiments, the pump is a peristaltic pump adapted to exercise peristaltic pumping when the tubing is mechanically stressed.

According to one embodiment the peristaltic pump comprises an epicyclic gear system comprising a plurality of planet gears and a central gear.

According to one embodiment, in the at least one pre-operational arrangement the planet gears are mechanically distressed and in the operational arrangement the planet gears and the tubing are mechanically stressed.

The rearrangement from said pre-operational arrangement to said operational arrangement may occur for example by an engaging movement of the central gear towards the planet gears which results in gear engagement between the central gear and the planet gears and at the same time in lateral displacement of the planet gears. Such a lateral displacement causes in turn pressure of at least one, e.g. two planet gears, on at least one segment of the tubing thereby achieving mechanical stress and functional peristaltic coupling. Alternatively, the central gear and the planet gears may be already engaged and the gear system may be adapted to be functionally couplable with the tubing by moving the gear system towards the tubing such as to press against the tubing, e.g. with two planet gears or by moving the tubing against the planet system, e.g. by pushing the tubing from the opposite side.

According to one embodiment, the epicyclic gear system comprises a planet gear holder for holding the planet gears and adapted to co-revolve with the planet gears when the planet gears revolve around the central gear.

According to one embodiment, in the at least one pre-operational arrangement the planet gear holder holds the planet gears and the tubing mechanically distressed and in the operational arrangement the planet gear holder cooperates with the central gear to hold the planet gears and the tubing mechanically stressed.

When the planet gears are functionally coupled to the tubing, revolving of the planet gears around the central gear results in peristaltic pumping.

According to certain embodiments the pump comprises a ratchet pump system comprising a wrench comprising a ratchet gear functionally coupled to a peristaltic wheel holder via a pawl.

According to one embodiment the peristaltic wheel holder is rotatable only in one direction by movement of the wrench about a pivotal axis. According to one embodiment the wrench is alternately movable between a first position and a second position.

According to one embodiment the peristaltic wheel holder comprises a plurality of peristaltic wheels for exercising peristaltic pumping on the tubing when the peristaltic wheel holder is rotating.

According to certain embodiments the pump comprises a piston pumping system comprising a plurality of pistons, rods, bars, pins or the like adapted as tubing push elements. In particular the tubing push elements may be adapted to alternately and repeatedly apply mechanical stress on different segments of the tubing respectively, thereby achieving peristaltic pumping.

The device may comprise a clamp movable from an open status, in which the tubing is mechanically distressed, to a closed status in which the tubing is mechanically stressed. In particular, the clamp may be adapted to rearrange from the open status into the closed status when the device is rearranged from the at least one pre-operational arrangement into the operational arrangement, thereby achieving functional peristaltic coupling of the tubing. This could be achieved for example by arranging the tubing between the clamp and the planet gears or peristaltic wheels so that the clamp in the closed status squeezes the tube in between, thus resulting in functional peristaltic coupling between the tubing and at least one planet gear or at least one peristaltic wheel, e.g. at least two planet gears or at least two peristaltic wheels.

According to certain embodiments, in the at least one pre-operational arrangement the tubing is fluidically disconnected from the reservoir and/or from the infusion element and in the operational arrangement the tubing is fluidically connected to the reservoir and to the infusion element. Fluidically disconnecting the tubing from the reservoir is one way of disconnecting the reservoir from the pump.

The term "fluidically disconnected" is used herein to indicate that passage of fluid is prevented. This pre-operational condition may be achieved e.g. by a physical disconnection, e.g. unplugged condition, of the tubing from the reservoir and/or the infusion element or from an occlusion of the fluid passage, e.g. by compression of the tubing, valve mechanism or equivalent fluid obstruction. A fluidically disconnected tubing may have the advantage of isolating the medicament within the reservoir in case the reservoir is pre-loaded with the medicament, thus preventing evaporation and/or crystallization of the medicament within the tubing or the infusion device, and thus extending the shelf life of the device. Also, in case chemical- and/or bio-compatibility between the medicament and the material of tubing is an issue for prolonged periods of time, confining the medicament within the reservoir fluidically disconnected from the tubing may be advantageous. Another advantage of a reservoir fluidically disconnected from the tubing, e.g. in case of using a collapsible/expandable pouch as reservoir, is that the reservoir may be loaded with the medicament without generating gas pressures within the device or encountering resistances, e.g. if no vent is present in order to seal the medicament from the environment.

The term "fluidically connected" is used herein to indicate that passage of fluid is enabled. This operational condition may be achieved e.g. by a physical connection, e.g. plugging, of the tubing to the reservoir and/or the infusion element or by the removal of an occlusion of the fluid passage.

The device may comprise a fluidic connector switchable from an occluding mode or disconnected mode, in which the reservoir and the tubing are fluidically disconnected, to an open mode or connected mode, in which the reservoir and the tubing are fluidically connected. For example, the fluidic connector may be of the plug-socket type or septum-piercer type or on/off valve type or tube pusher type adapted e.g. as a rod, bar or clamp-like occluder capable of applying pressure on the tubing. In alternative or in addition, the device may comprise a fluidic connector of any of these types switchable from an occluding mode or disconnected mode, in which the tubing and the infusion element are fluidically disconnected, to an open mode or connected mode, in which the tubing and the infusion element are fluidically connected.

According to certain embodiments, in the at least one pre-operational arrangement the reservoir is fluidically accessible from the outside of the device via a filling port so that medicament can be introduced into the reservoir through the port and in the operational arrangement the reservoir is inaccessible from the outside of the device so that medicament is prevented from being introduced into the reservoir, e.g. by making the filling port no longer accessible or no longer capable of allowing passage of medicament to the inside of the reservoir, e.g. by occlusion or other form of closure. According to one operational arrangement, the reservoir is prevented from being removed from the device and eventually to be replaced. According to one embodiment, the reservoir is still fluidically accessible from the outside of the device when the device is in the operational arrangement but the filling port is at a location which allows loading of the medicament only in a pre-operational arrangement. For example, the filling port may be located on an adhesive side of the device to be attached to the skin of a patient, wherein the reservoir is loaded with the medicament before attaching the device to the skin and wherein removal of the device from the skin to access the filling port would cause irreversible removal of the infusion element from the skin. In such a case re-loading the reservoir with a medicament would be anyway useless as the infusion element cannot be reinserted into the skin and the device cannot be reused.

According to one embodiment the following pre-operational conditions are changed into respective operational conditions in the rearrangement from a pre-operational arrangement into the operational arrangement. In particular, in the pre-operational arrangement the tubing is mechanically distressed, whereas in the operational arrangement the tubing is mechanically stressed, respectively. Also, in the pre-operational arrangement the reservoir is fluidically accessible from the outside of the device via a filling port so that medicament can be introduced into the reservoir through the port or the reservoir is preloaded with the medicament and adapted to be introduced or attached to the medical device, whereas in the operational arrangement the reservoir is inaccessible from the outside of the device so that medicament is prevented from being introduced into the reservoir and the reservoir is prevented from being removed from the device.

According to one embodiment, the following further pre-operational condition is changed into a respective operational condition in the rearrangement from a pre-operational arrangement into the operational arrangement. In particular, in the pre-operational arrangement the tubing is fluidically disconnected from the reservoir and/or from the infusion element, whereas in the operational arrangement the tubing is fluidically connected to the reservoir and to the infusion element.

According to certain embodiments, the device comprises at least one reservoir push element adapted to push a volume of medicament out of the reservoir, which fills at least a part of the inner volume of the tubing and/or of the infusion element when the device is rearranged from the at least one pre-operational arrangement into the operational arrangement. According to one embodiment the volume of medicament pushed out of the reservoir slightly exceeds the sum of the inner volume of the tubing and of the infusion element such that e.g. at least a drop of medicament can be observed coming out of the infusion element. In such a way priming of the device, i.e. filling of the liquid transportation conduits such as tubing and infusion element, with the medicament, can be achieved at least in part as a result of the rearrangement of the device from a pre-operational arrangement into the operational arrangement. The reservoir push element may be embodied as a pin, rod, bar or surface capable of applying pressure on the reservoir.

The embodiments comprising a reservoir push element may be more suitable together with certain types of pumps such as e.g. a membrane pump, wherein the pump may be embodied e.g. as comprising a chamber comprising a membrane and two valves adapted to alternately open in accordance with the movement of the membrane such as to direct the flow of medicament from the reservoir towards the infusion element through the chamber. In alternative or in addition priming may occur, e.g. completed, by operation of the pump in the operational arrangement, regardless of the type of pump used. Another possibility, regardless of the type of pump, is that priming is achieved as the result of the rearrangement from a first pre-operational arrangement into a second pre-operational arrangement before the device becomes operational by a further rearrangement into the operational arrangement.

According to certain embodiments the device is adapted to be placed in contact with the skin of a patient in a pre-operational arrangement wherein the infusion element is displaceable such as to penetrate the skin as a result of the rearrangement from the pre-operational arrangement to the operational arrangement while being in contact with the skin. This could be achieved for example by triggering a triggering element coupled to the infusion element by the rearrangement of the device components. This could be also achieved by simply extending the infusion element, as a result of the displacement of device components, from a retracted position inside the device, e.g. a cavity of the device, to an extracted position such as to protrude from the device and penetrate the skin to a controlled depth. The device may be advantageously adapted in such cases so that the priming is carried out in advance, i.e. in a pre-operational arrangement. In particular, there might be as above two pre-operational arrangements, wherein the device is adapted to rearrange from a first pre-operational arrangement to a second pre-operational arrangement wherein priming may be achieved during such rearrangement, e.g. by a reservoir push element, or in the second pre-operational arrangement, in which e.g. the tubing is functionally coupled to the pump and the pump can thus be operated, and wherein a further rearrangement into the operational arrangement is then required, e.g. to penetrate the skin with the infusion element.

According to certain embodiments, the rearrangement from the at least one pre-operational arrangement to the operational arrangement is irreversible. This can be advantageous especially to prevent misuse. The term "irreversible" is herein used to indicate that any attempt to return from the operational arrangement to a pre-operational arrangement would result in undue effort, i.e. significantly bigger effort compared to the reverse action of changing from a pre-operational arrangement to the operational arrangement, and would eventually result in damage of the device.

The present invention refers also to kit, e.g. a ready to assemble kit, comprising a plurality of components adapted to be assembled together such as to form the device in a pre-operational arrangement. In particular, the components of the kit are designed to engage with each other in a specific manner as building blocks such as to assume a first stable arrangement corresponding to the pre-operational arrangement. This can be achieved e.g. by complementary or matching shapes, guiding elements, reference signs, etc. . . . The term "kit" refers to either a single group of components, e.g. packaged together, or separate groups of components, e.g. packaged and acquirable separately, each comprising one or more components adapted to be assembled together such as to form the device in a pre-operational arrangement. For example, a kit may comprise a first component comprising the pump and the tubing and a second component comprising the reservoir, wherein the reservoir may be pre-loaded with the medicament or adapted to be loaded with the medicament and may be manufactured and packaged separately from the first component. The reservoir may be a separate component e.g. adapted to fit between a first component and a second component.

The present invention refers also to a method of manufacturing device components adapted to be assembled in a pre-operational arrangement. According to one embodiment the method comprises assembling the device into a pre-operational arrangement.

According to one embodiment the method comprises loading a medicament in the reservoir before or after loading the reservoir in the device.

More in detail the present invention is explained with reference to the following drawings representing exemplary embodiments.

FIG. 1a is an exploded view of a medical device 100 for trans-dermal infusion of a medicament. FIG. 1b is an exploded view of the same device components of FIG. 1a seen from a different perspective, i.e. upside down. The medical device 100 comprises a housing 10 comprising a base 11 and a cover 16. Attached to the external surface of the base 11 is an adhesive layer 90 suitable for remobably fix the device 100 to the skin of a patient. The adhesive layer 90 is covered by a covering layer 91 to be peeled before use.

The base 11 comprises features such as protrusions 12 and slits 13 adapted to match at least in part respective complementary features 17, 18 of the cover 16. In particular, these features 12, 13, 17, 18 guide the alignment of the base 11 and the cover 16 until a first stop position is reached, which corresponds to a pre-operational arrangement of the device 100, and in a second step guide the rearrangement in the operational arrangement until a second stop position is reached, wherein only movement from the first stop position to the second stop position is allowed and not vice versa. The medical device 100 further comprises a reservoir 20 for holding a medicament to be infused. The reservoir 20 is a collapsible pouch comprising a filing port 21 and an outlet port 22. The base 11 comprises an inner space 14 to accommodate the reservoir 20 and an aperture 15, wherein the filling port 21 is aligned with the aperture 15.

The medical device 100 further comprises a peristaltic pump 50 and a diaphragm 80 separating the reservoir 20 from the pump 50. The pump 50 comprises an epicyclic gear system comprising three planet gears 51, each having a stem 57, a central gear rotor 52 comprising a central gear 53, a planet gear holder 54 for holding the planet gears 51. In particular, the planet gear holder 54 comprises three recesses 55 and three holes 56 so that each planet gear 51 can sit in a recess 55 with the stem 57 in a hole 56, and each stem 57 is secured in place by a fastener 58 located on the opposite side of each hole 56. More in detail, each hole 56 is elongated radially outwards so that each stem 57 can slide radially across the hole 56. The pump 50 further comprises a tubing 40 fluidically connected at one end with the reservoir 20 via outlet port 22 and at the other end with an infusion element 30. The planet gears 51 are functionally couplable to the tubing 40, i.e. adapted to alternately apply mechanical stress to segments of the tubing 40 as they rotate along the tubing 40. Since the tubing 40 is fixed, rotation of the planet gears 51 about their stems 57 results in revolving of the planet gears 51 around the central gear 53 and co-revolving of the planet gear holder 54. The mechanical stress applied to the tubing 40 by the planet gears 51 as they rotate alternately along the tubing 40 results in peristaltic pumping of medicament from the reservoir 20 towards the infusion element 30 through the tubing 40.

The central gear rotor 52 comprises ferromagnetic elements 59 and a shaft 60 engageable with a safe-lock mechanism 70.

The central gear rotor 52 may rotate only together with the safe-lock mechanism 70 by engaging the safe-lock mechanism 70 with the shaft 60. The safe-lock mechanism 70 comprises a spring 71 in contact with the central gear rotor 52 and pushing the safe-lock mechanism 70 against the inner walls of the cover 16, wherein protrusions 73 prevent the safe-lock mechanism 70 and thus the central gear rotor 52 to rotate. The safe-lock mechanism 70 further comprises a magnet 72 facing the cover 16. The safe-lock mechanism 70 locks the central gear rotor 52 preventing it to rotate until a separate hand-held drive device (not shown) is placed in proximity of the medical device 100 and provides the specific energy required to unlock the safe-lock mechanism 70 and activate the pump 50. In particular, the drive device comprises an activation unit comprising an unlocking element comprising a magnet designed to interact with the magnet 72 of the safe-lock mechanism thereby providing energy for unlocking the safe-lock mechanism 70. The activation unit also comprises a magnetic drive unit designed to interact with the ferromagnetic elements 59 of the central gear rotor 52 thereby providing rotational force to the central gear rotor 52. In particular, the magnetic force of the unlocking element overcomes the force provided by the spring 71 and the safe-lock mechanism 70 is pushed downwards towards the central gear rotor 52, thus freeing the safe-lock mechanism 70 from the protrusions 73. Then the magnetic drive unit provides the central gear rotor 52 with the energy required to rotate and pump a specific dose of medicament. As soon as the requested dose has been infused, the drive unit stops to provide energy to the central gear rotor 52, which stops rotating. The safe-lock mechanism 70 is then locked again as soon as the unlocking element is removed or disabled. The combined effect of the unlocking element and the drive unit of the drive device on the safe-lock mechanism 70 and central gear rotor 52 respectively makes the activation of the pump 50 specific as a key.

Figure 1C:
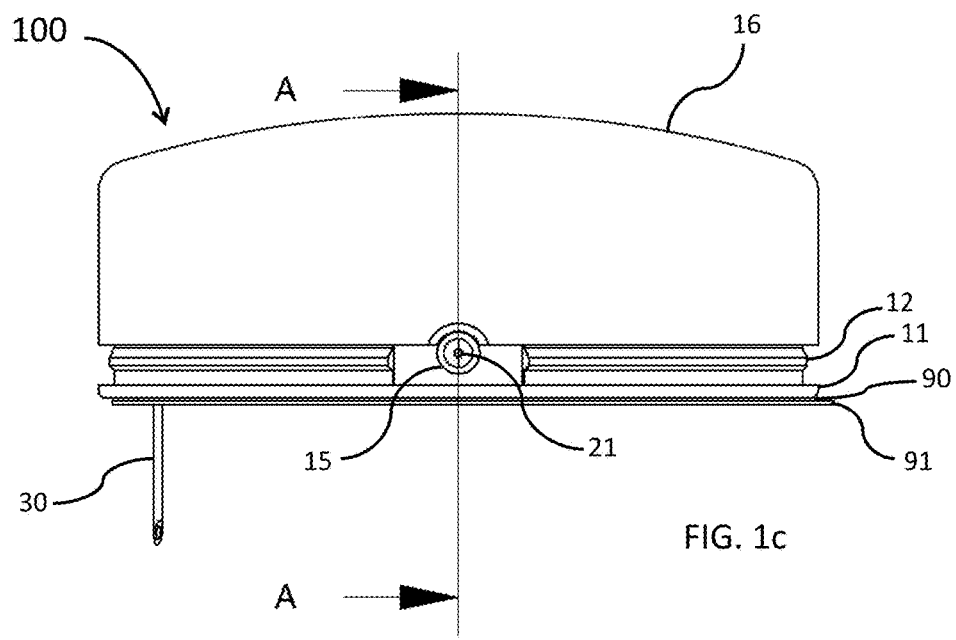
FIG. 1c shows the same device of FIG. 1a and FIG. 1b assembled in a pre-operational arrangement.
Figure 1D:
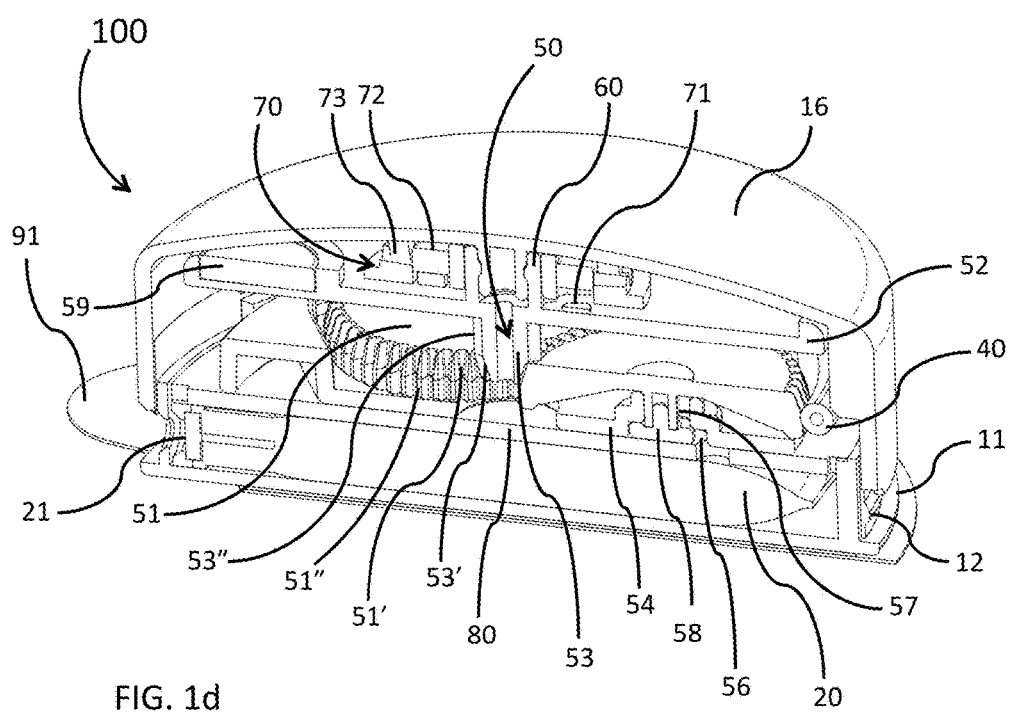
FIG. 1d is a perspective view of the device of FIG. 1c cut through section A-A such as to show the arrangement of the internal components in this pre-operational arrangement.

FIG. 1c shows the same device 100 of FIG. 1a and FIG. 1b assembled in a pre-operational arrangement with the base 11 and the cover 16 in a first position. FIG. 1d is a perspective view of the device 100 of FIG. 1c cut through section A-A such as to show the arrangement of the internal components in this pre-operational arrangement. It can be seen that the reservoir 20 is fluidically accessible from the outside of the device 100 via the filling port 21 so that medicament can be introduced into the reservoir 20 through the port 21. This corresponds to a first pre-operational condition. The reservoir 20 is shown in its expanded form already loaded with the medicament. Another pre-operational condition, which is met in this pre-operational arrangement, is that the pump 50 is in a mechanically distressed condition preventing functional operation of the pump 50. In particular, the planet gears 51 and the tubing 40 are mechanically distressed. This is because the central gear 53 is disengaged from the planet gears 51.

Figure 1E:
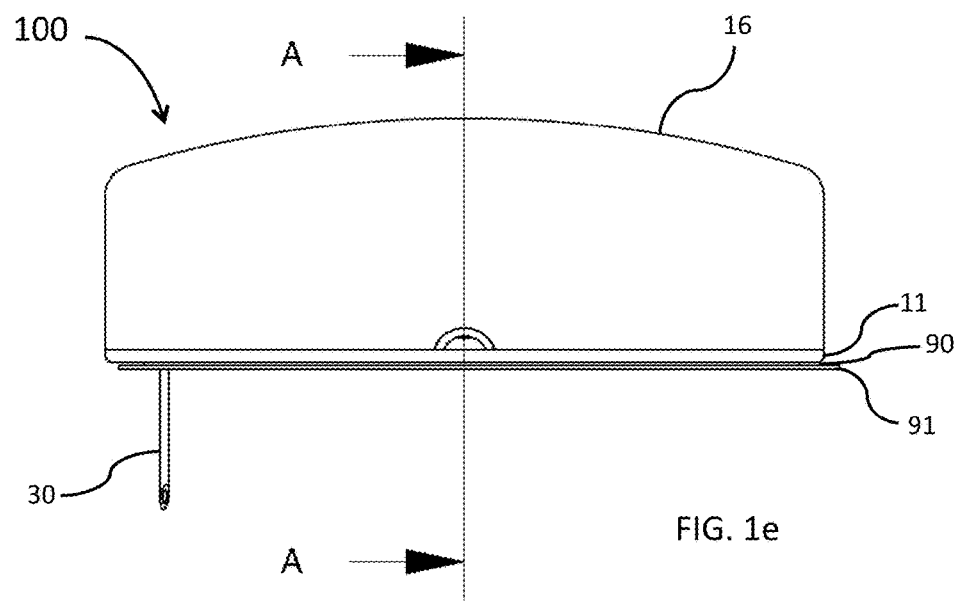
FIG. 1e shows the same device of FIG. 1c in the operational arrangement.
Figure 1F:
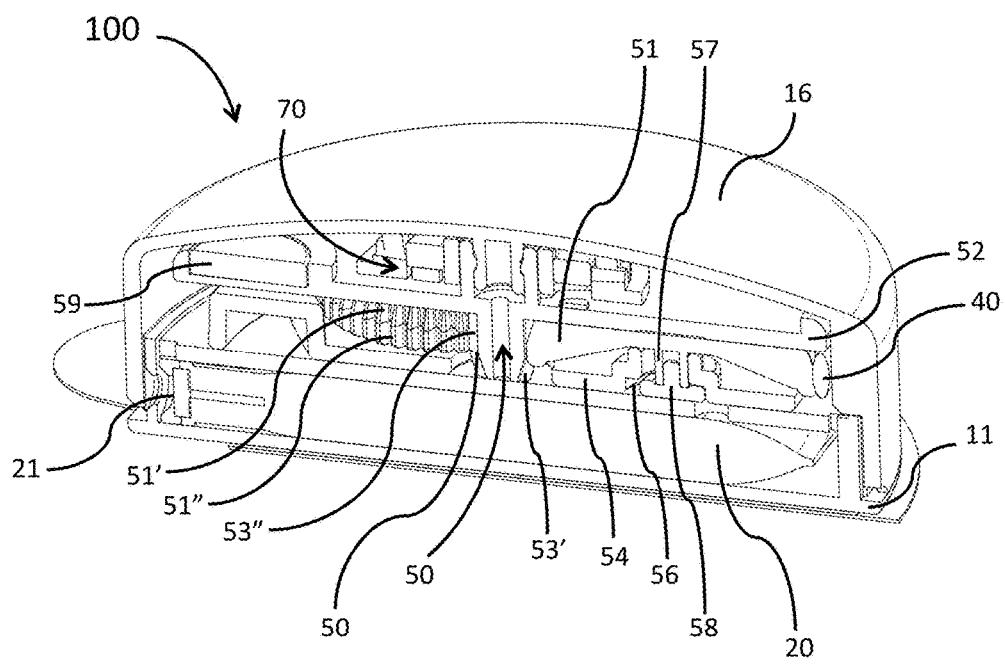
FIG. 1f is a perspective view of the device of FIG. 1e cut through section A-A such as to show the rearrangement of the internal components in the operational arrangement.

FIG. 1e shows the same device 100 of FIG. 1c in the operational arrangement obtained by biasing the base 11 and the cover 16 against each other in a second position. FIG. 1f is a perspective view of the device 100 of FIG. 1e cut through section A-A such as to show the rearrangement of the internal components in the operational arrangement. It can be seen that the reservoir 20 is inaccessible from the outside of the device 100 because the filling port 21 is no longer accessible. In such a way medicament is prevented from being introduced into the reservoir 20, e.g. when the reservoir 20 is empty. Also, the pump 50 is now in a mechanically stressed condition enabling functional operation of the pump 50. In particular, the planet gears 51 and the tubing 40 are mechanically stressed. It can be seen that the central gear 53 is engaged with the planet gears 51 and the planet gears 51 are radially displaced through the elongated holes 56 such as to squeeze the tubing 40.

In order to make the rearrangement from the pre-operational arrangement to the operational arrangement easier, the planet gears 51 have a geared planet edge comprising a wedged planet edge part 51' tapering towards the top and a lower straight planet edge part 51" as shown in the FIGS. 1d and 1f. The central gear 53 also has a wedged central gear part 53' tapering towards the bottom and an upper straight central gear part 53" above the wedges central gear part 53'. In particular, in the pre-operational arrangement, the wedged central gear part 53' fits between the wedged planet gear parts 51' of the planet gears 51. In this arrangement, there is no or minimal mechanical stress between the central gear 53 and the planet gears 51 and between the planet gears 51 and the tubing 40. As the device 100 is rearranged into the operational arrangement, the central gear 53 is pushed down (with reference to the figures) in between the planet gears 51 so that the straight central gear part 53" becomes in contact with the straight planet edge parts 51" thereby forcing the planet gears 51 to displace radially outwards by sliding through the elongated holes 56 of the planet gear holder 54 and establishing a mechanically stressed engaged relationship between the central gear 53 and the planet gears 51 and between the planet gears 51 and the tubing 40.

Only in this operational arrangement the device 100 is operational, i.e. capable of proper operation by interaction with the separate hand-held drive device as described above.

Figure 2A:
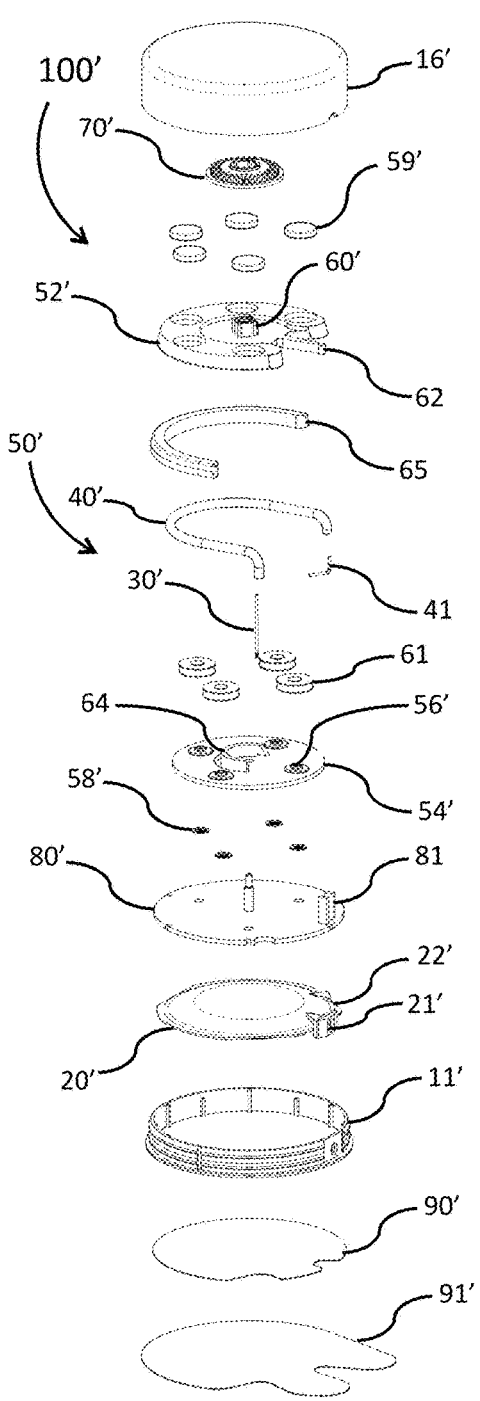
FIG. 2a and FIG. 2b are exploded views of a variant of the medical device of FIG. 1a and FIG. 1b wherein the device components are seen from different perspectives respectively.
Figure 2B:
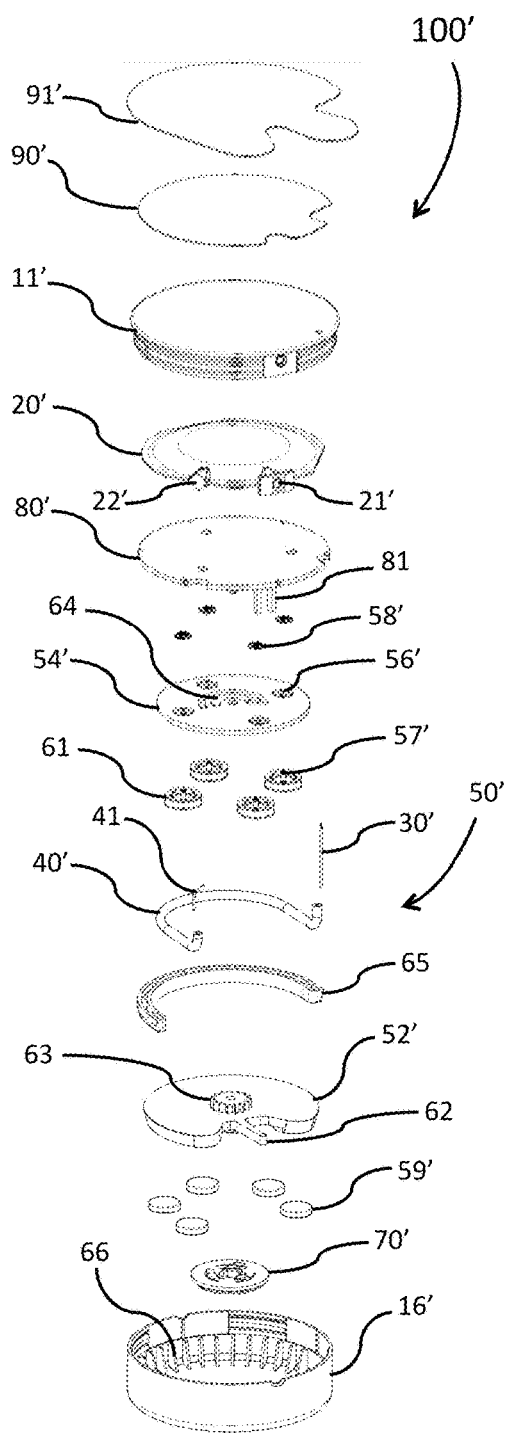

FIG. 2a is an exploded view of a medical device 100', which is a variant of the medical device 100 of FIG. 1a-1f. FIG. 2b is an exploded view of the same device components of FIG. 2a seen from a different perspective, i.e. upside down. To avoid repetition, not all elements are described in detail. The medical device 100' comprises a base 11' and a cover 16' similar to that of the device 100. The cover 16' comprises on one internal side wedged push features 66, whose function is better understood with reference to FIG. 2e and FIG. 2g. Attached to the external surface of the base 11' is an adhesive layer 90' covered by a covering layer 91' similar to adhesive layer 90 and cover layer 91 respectively. The medical device 100' further comprises a reservoir 20' similar to reservoir 20 comprising a filing port 21' and an outlet port 22'. The medical device 100' further comprises a peristaltic pump 50' and a diaphragm 80' separating the reservoir 20' from the pump 50'. The pump 50' is different from pump 50. The pump 50' is a ratchet pump system comprising four peristaltic wheels 61, each having a stem 57', and a wrench 52' comprising a ratchet gear 63 functionally coupled to a peristaltic wheel holder 54' via a pawl 64. In particular, the peristaltic wheel holder 54' comprises four holes 56' so that each peristaltic wheel 61 is inserted with the stem 57' in a hole 56', and each stem 57' is secured in place by a fastener 58' located on the opposite side of each hole 56'. The pump 50' further comprises a tubing 40' fluidically connected at one end with the reservoir 20' via outlet port 22' and fluid connector 41 and at the other end with an infusion element 30'. The peristaltic wheels 61 are functionally couplable to the tubing 40', i.e. adapted to alternately apply mechanical stress to segments of the tubing 40' as they rotate along the tubing 40'. The wrench 52' further comprises an appendix 62, a shaft 60' and recesses to accommodate ferromagnetic elements 59'. The shaft 60' is engageable with a safe-lock mechanism 70' similar to the safe-lock mechanism 70 described above, wherein the wrench 52' may rotate only together with the safe-lock mechanism 70' by engaging the safe-lock mechanism 70' with the shaft 60' when the safe-lock mechanism 70' is unlocked and when rotational force is inductively provided to the ferromagnetic elements 59' by the activation unit of the separate hand-held device (not shown).

In particular, the peristaltic wheel holder 54' is rotatable only in one direction by movement of the wrench 52' about a pivotal axis, i.e. an axis passing through the center of the shaft 60'. More in detail, the wrench 52' is alternately rotatable between a first position and a second position provided by two stoppers 81 on the diaphragm 80', between which the appendix 62 is located. By applying an alternated magnetic field to the ferromagnetic elements 59' the appendix 62 is moved back and forth between the stoppers 81. At each cycle the pawl is advanced in one direction of one step corresponding to the next interdigital space of the ratchet gear 63. Therefore at each cycle the peristaltic wheel holder 54' rotationally advances in one direction.

The device 100' comprises also a clamp 65 movable from an open status, in which the tubing 40' is mechanically distressed, to a closed status in which the tubing 40' is mechanically stressed.

Figure 2C:
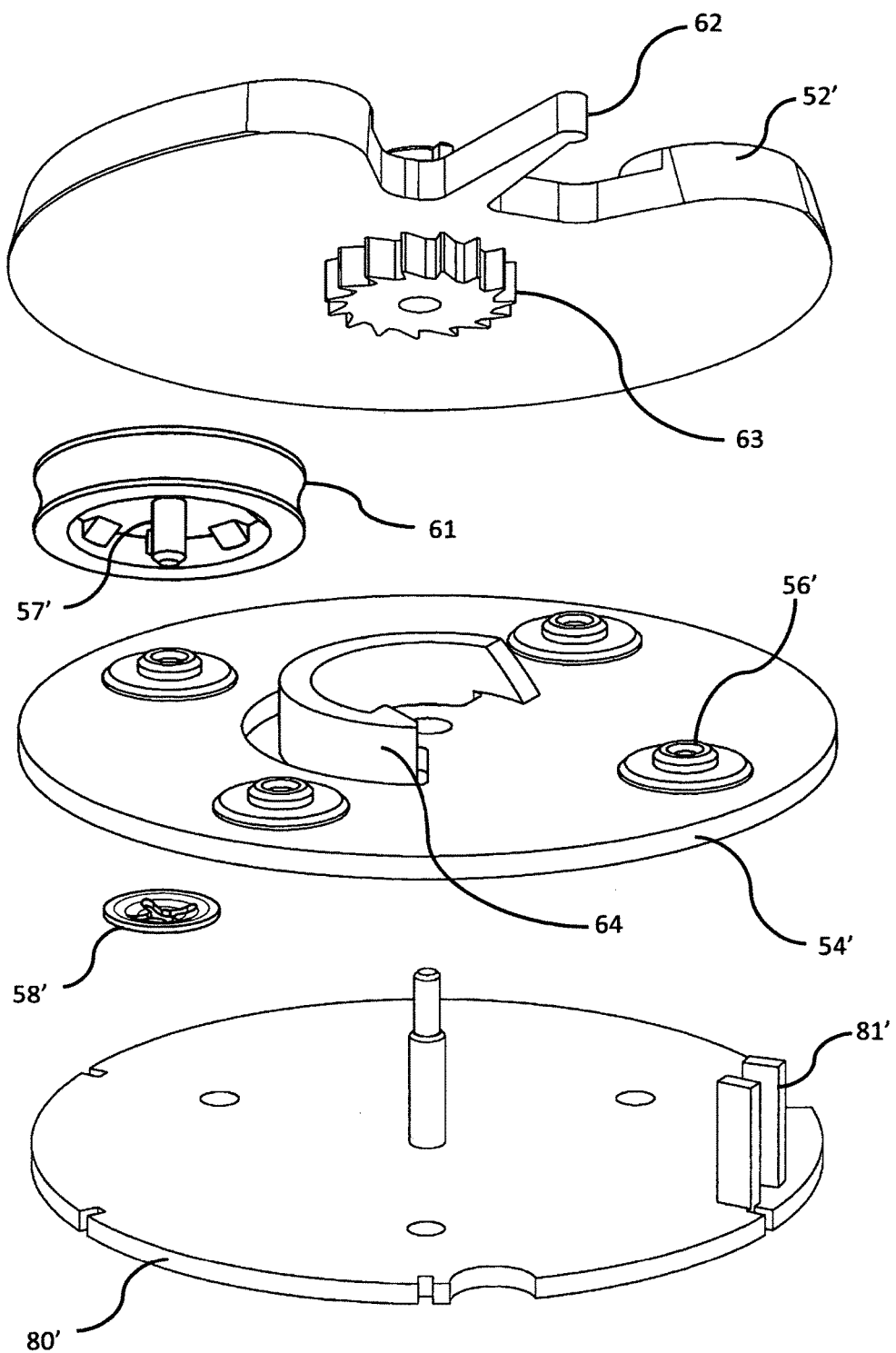
FIG. 2c shows some components of FIGS. 2a and 2b in more detail.

The mechanism of the ratchet pump system can be better understood with reference to FIG. 2c, which indicates the relationship between the wrench 52', the peristaltic wheel holder 54' and the diaphragm 80' in greater detail and magnification.

Figure 2D:
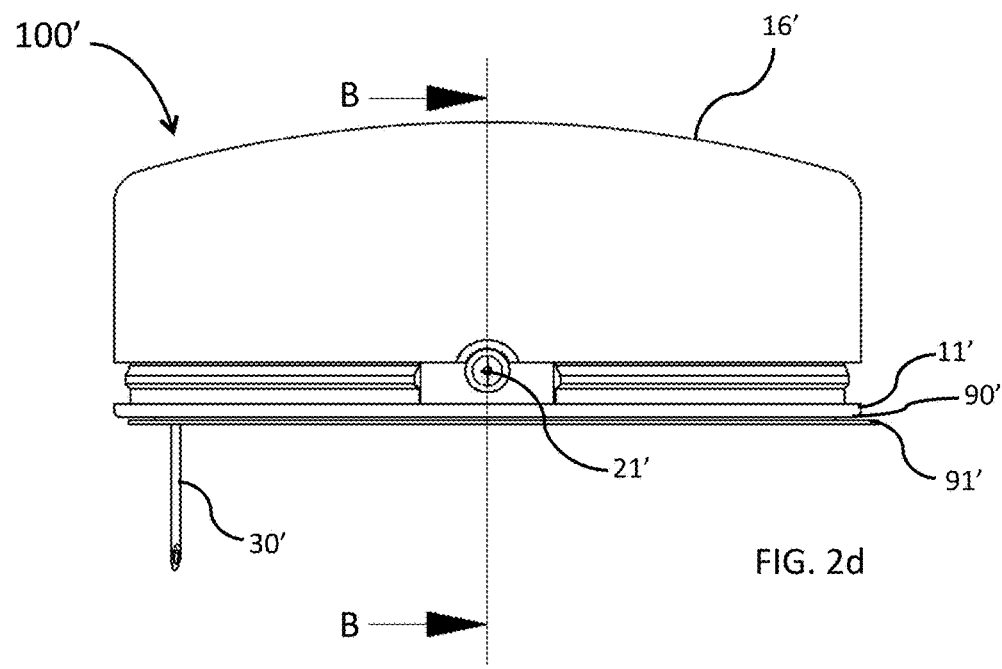
FIG. 2d shows the same device of FIG. 2a and FIG. 2b assembled in a pre-operational arrangement.
Figure 2E:
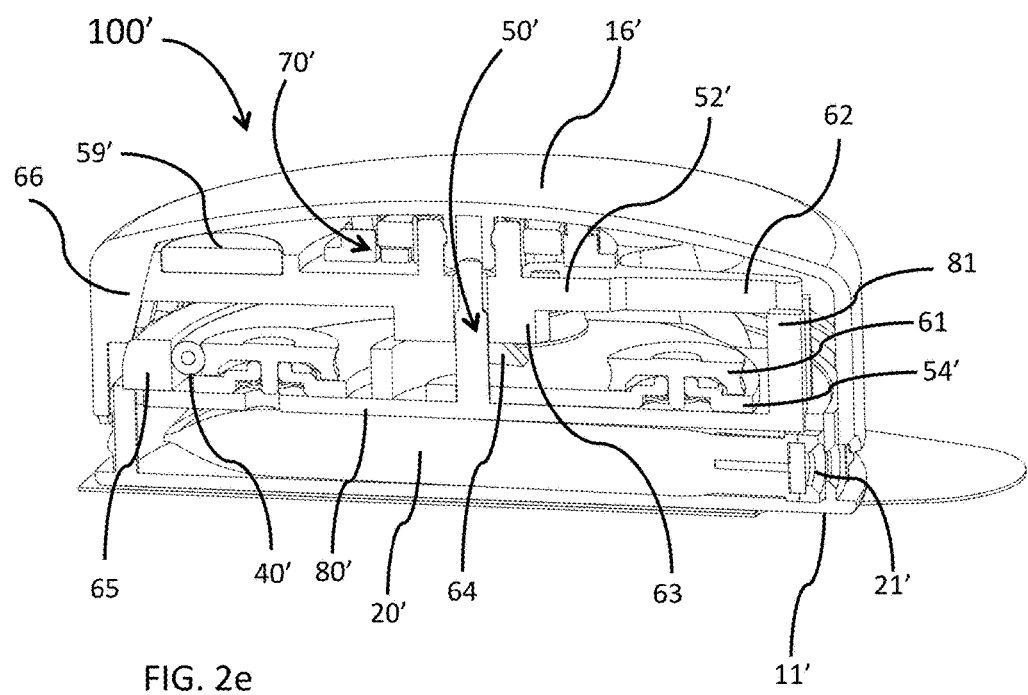
FIG. 2e is a perspective view of the device of FIG. 2d cut through section B-B such as to show the arrangement of the internal components in this pre-operational arrangement.

FIG. 2d shows the same device 100' of FIG. 2a and FIG. 2b assembled in a pre-operational arrangement with the base 11' and the cover 16' in a first position. FIG. 2e is a perspective view of the device 100' of FIG. 2d cut through section B-B such as to show the arrangement of the internal components in this pre-operational arrangement. It can be seen that the reservoir 20' is fluidically accessible from the outside of the device 100' via the filling port 21' so that medicament can be introduced into the reservoir 20' through the port 21'. This corresponds to a first pre-operational condition. The reservoir 20' is shown in its expanded form already loaded with the medicament. Another pre-operational condition, which is met in this pre-operational arrangement, is that the pump 50' is in a mechanically distressed condition preventing functional operation of the pump 50'. In particular, the tubing 40' is mechanically distressed and the pawl 64 is disengaged from the ratchet gear 63.

Figure 2F:
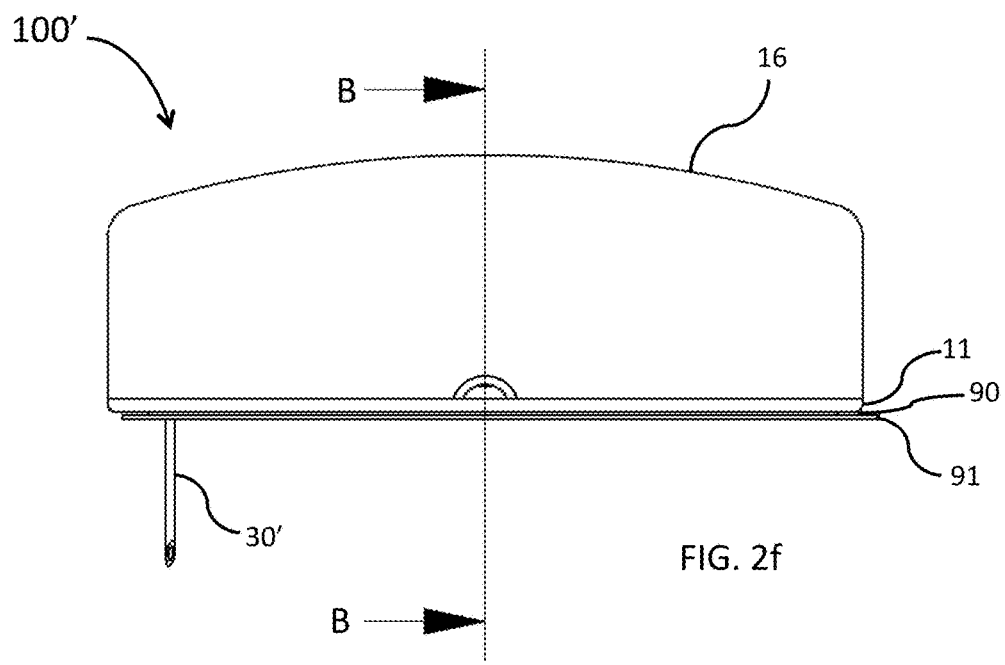
FIG. 2f shows the same device of FIG. 2d in the operational arrangement.
Figure 2G:
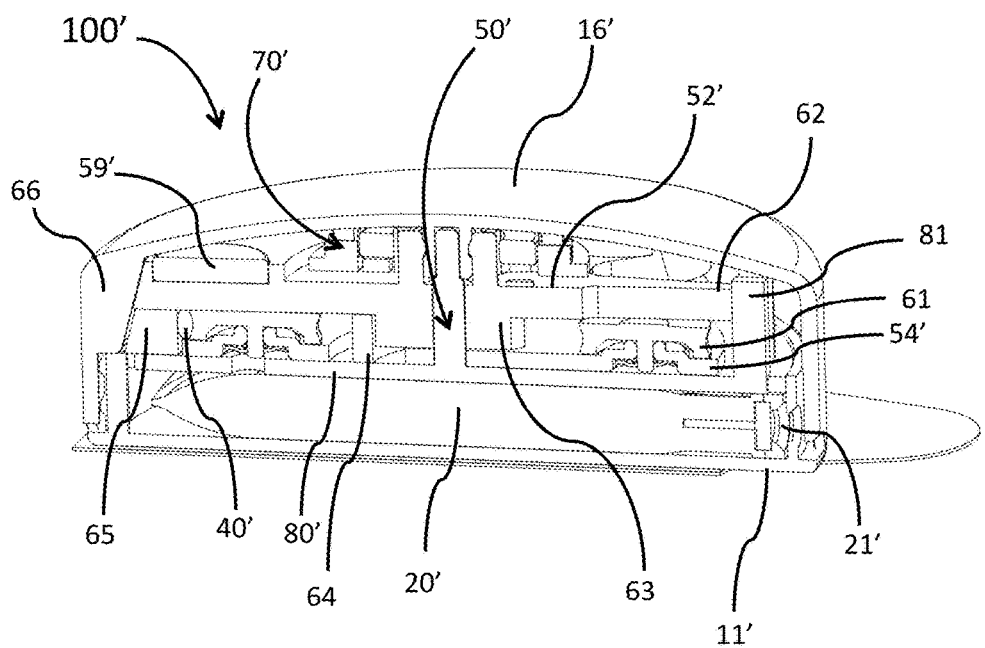
FIG. 2g is a perspective view of the device of FIG. 2f cut through section B-B such as to show the rearrangement of the internal components in the operational arrangement.

FIG. 2f shows the same device 100' of FIG. 2d in the operational arrangement obtained by biasing the base 11' and the cover 16' against each other in a second position. FIG. 2g is a perspective view of the device 100' of FIG. 2f cut through section B-B such as to show the rearrangement of the internal components in the operational arrangement. It can be seen that the reservoir 20' is inaccessible from the outside of the device 100' because the filling port 21' is no longer accessible. In such a way medicament is prevented from being introduced into the reservoir 20', e.g. when the reservoir 20' is empty. Also, the pump 50' is now in a mechanically stressed condition enabling functional operation of the pump 50'. In particular, the tubing 40' is mechanically stressed and the pawl 64 is engaged with the ratchet gear 63. Mechanical stress of the tubing 40' is achieved by movement of the clamp 65 from the open status of FIG. 2e to the closed status of FIG. 2g caused by the wedged push features 66 of the cover 16', which push the clamp 65 radially inwards such as to squeeze the tubing 40' between the clamp 65 and a peristaltic wheel 61.

In this operational arrangement, rotation of the peristaltic wheel holder 54' results in rotation and advancement along the tubing 40' of the peristaltic wheels 61 coupled to the tubing 40', which results in peristaltic pumping of medicament from the reservoir 20' towards the infusion element 30' through the tubing 40'.

Instead of the ratchet pump system like that shown in FIGS. 2a to 2g the pump 50' may comprise a continuously rotatable peristaltic wheel holder, e.g. functionally coupled to a rotor similar e.g. to central gear rotor 52 instead of wrench 52'. In alternative the peristaltic wheel holder may be adapted as a rotor capable of receiving rotational force directly from a hand-held drive device or from a motor.

Figure 3A:
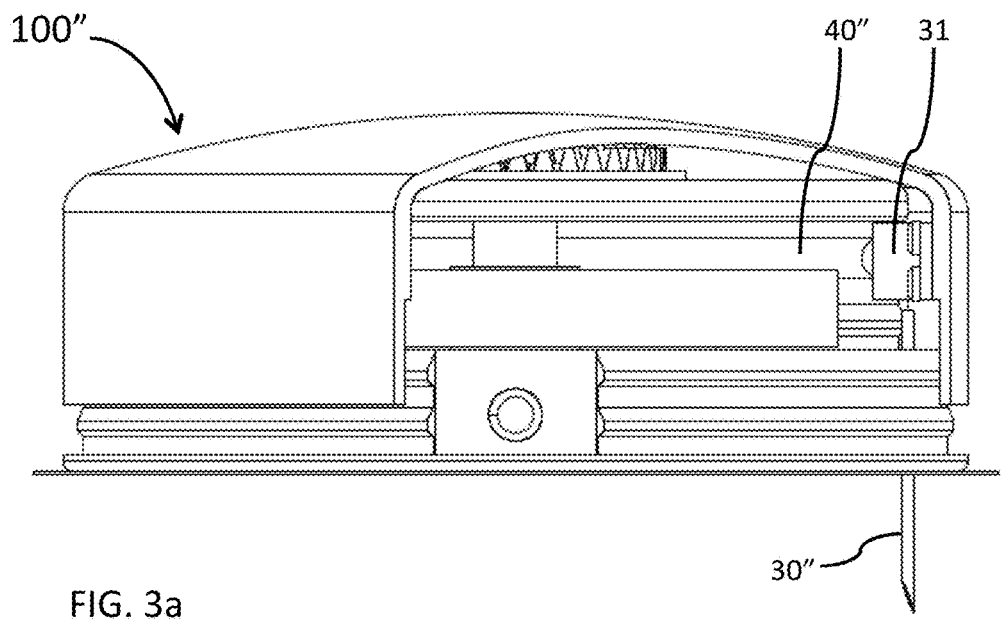
FIG. 3a and FIG. 3b show an embodiment with a fluidic connector in the pre-operational arrangement and in the operational arrangement respectively (several components removed or simplified for clarity).
Figure 3B:
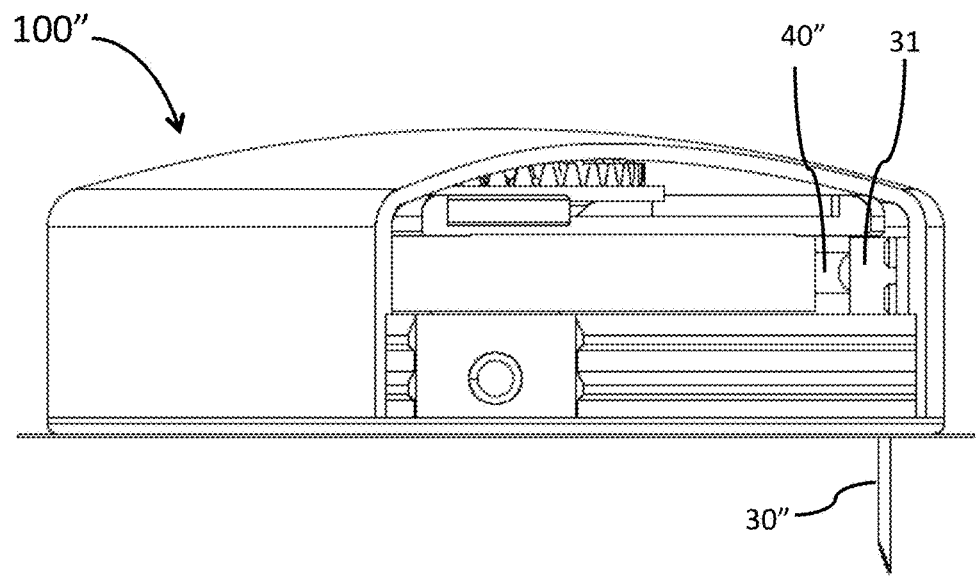

FIG. 3a and FIG. 3b show another example of medical device 100" similar to the devices 100, 100' of the previous examples. In particular, FIG. 3a shows the device 100" in the pre-operational arrangement and FIG. 3b shows the device 100" in the operational arrangement, wherein several components including part of the housing have been removed or simplified for clarity of illustration. One particular feature of the device 100" is a fluidic connector 31 of the plug-socket type for fluidically connecting one end of the tubing 40" to the infusion element 30". In particular, in the pre-operational arrangement the tubing 40" and the infusion element 30" are fluidically disconnected and in the operational arrangement the tubing 40" and the infusion element 30" are fluidically connected.

Figure 4A:
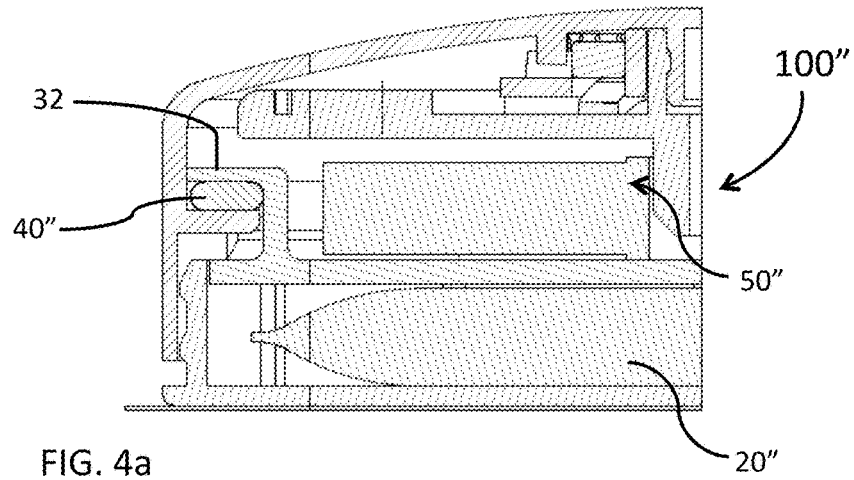
FIG. 4a to FIG. 4c show an embodiment with another type of fluidic connector (several components removed or simplified for clarity).
Figure 4B:
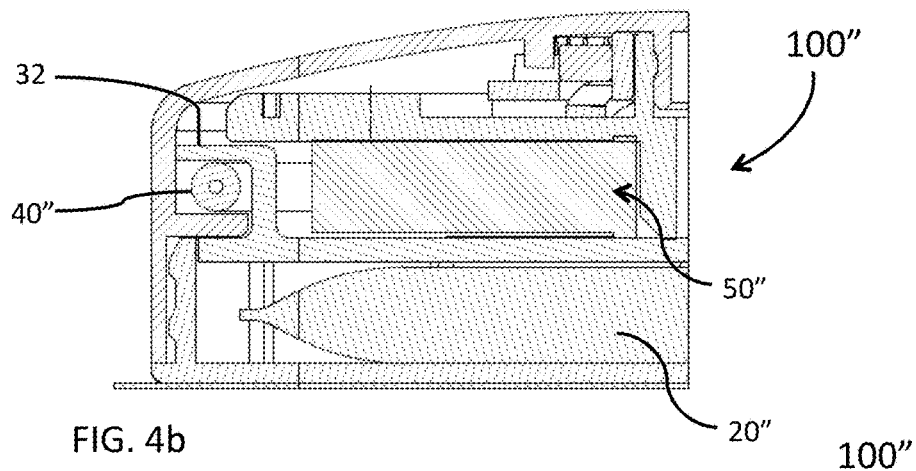
Figure 4C:
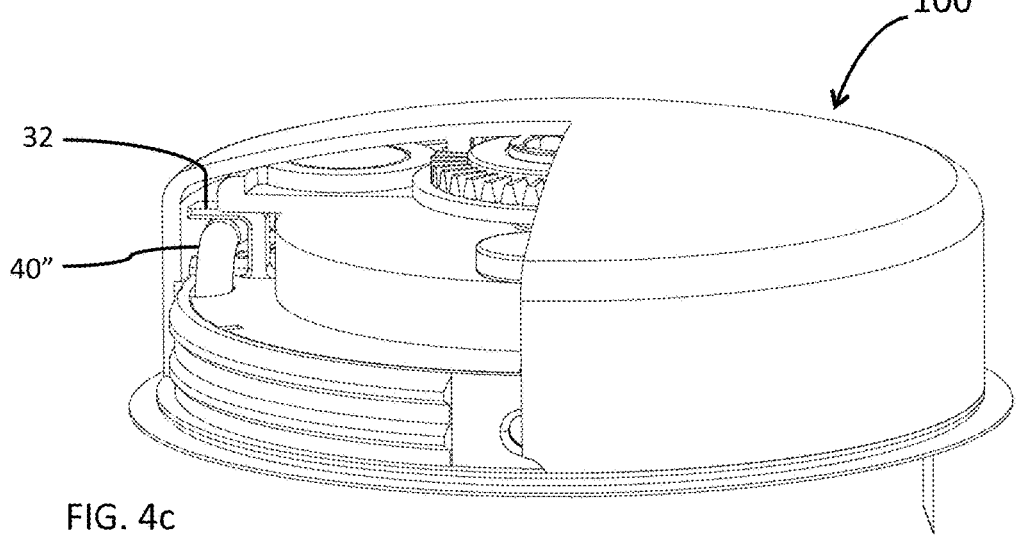

FIG. 4a to FIG. 4c show another feature of device 100" of FIG. 3a and FIG. 3b with another type of fluidic connector 32 for fluidically connecting the reservoir 20" and the tubing 40". In particular, FIG. 4a partially shows in cross-section the device 100" in the pre-operational arrangement. FIG. 4b partially shows in perspective the device 100" in the operational arrangement. The fluidic connector 32 is of the tube pusher type adapted as a clamp-like occluder capable of applying pressure on the tubing 40" thereby fluidically disconnecting the reservoir 20" from the pump 50". In particular, the fluidic connector 32 is switchable from an occluding mode, in which the reservoir 20" and the tubing 40" are fluidically disconnected, to an open mode, in which the reservoir 20" and the tubing 40" are fluidically connected, as the device 100" is rearranged from the pre-operational arrangement into the operational arrangement.

Although the fluidic connectors 31, 32 are shown with reference to the same device 100", they do not necessarily need to be present together on the same device or be of different types. The examples given are for illustrative purpose only.

Figures 5A, 5B, 5C:
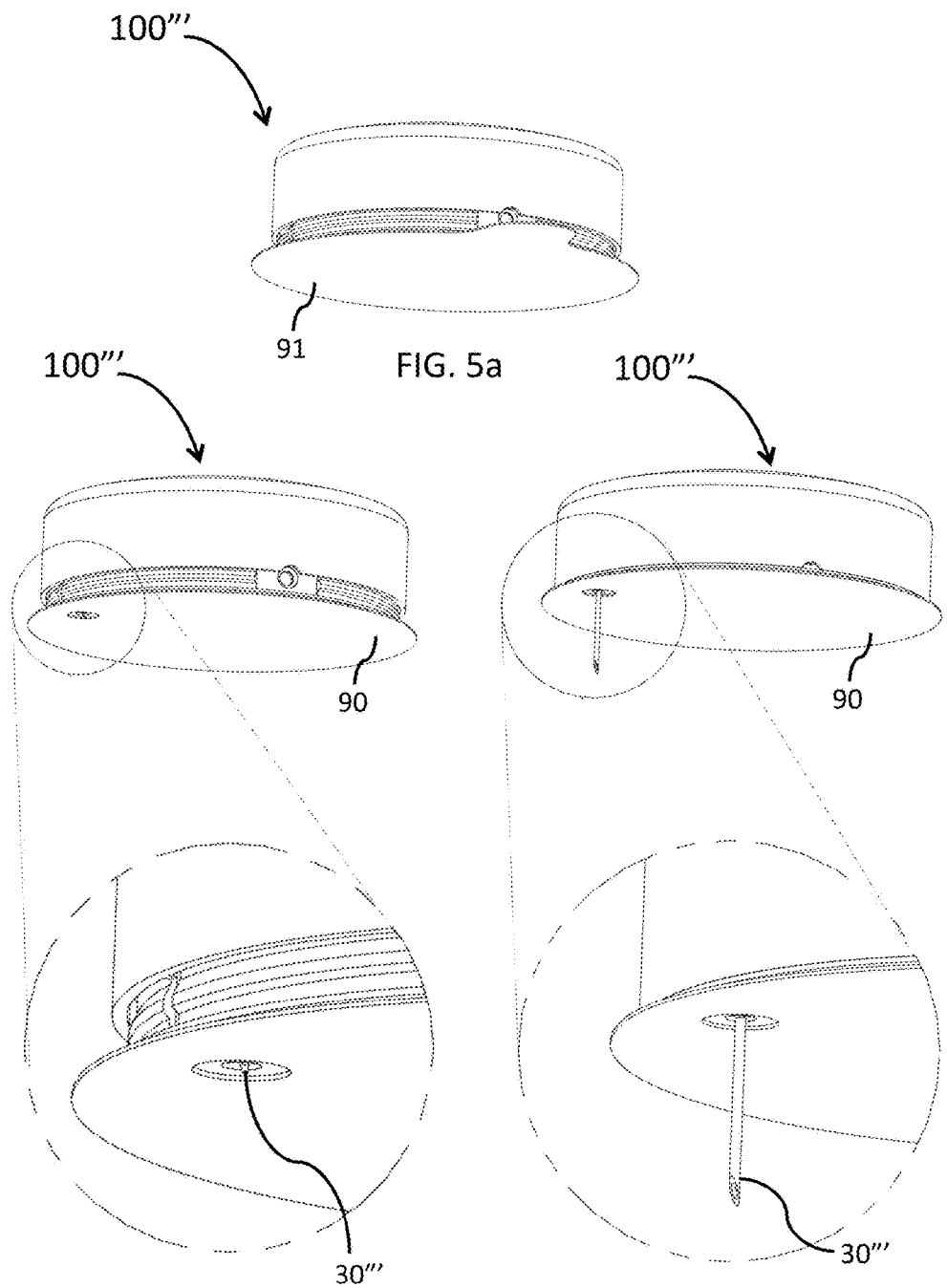
FIGS. 5a to 5c show an embodiment comprising a displaceable infusion element.

FIG. 5a to FIG. 5c show another example of medical device 100''' similar to the devices 100, 100', 100", and comprising a displaceable infusion element 30'''. In particular, FIG. 5a shows the device 100''' in the pre-operational arrangement with the cover layer 91 covering the adhesive layer 90 and the infusion element 30'''. FIG. 5b shows the device 100''' of FIG. 5a with the cover layer 91 removed such as to show the infusion element 30''' in a refracted position (detail magnified). FIG. 5c shows the device 100''' of FIG. 5b in the operational arrangement, wherein the infusion element 30''' is in an extracted position (detail magnified). The device 100''' is thus adapted to be placed in contact with the skin of a patient in the pre-operational arrangement wherein the infusion element 30''' is displaceable such as to penetrate the skin as a result of the rearrangement from the pre-operational arrangement to the operational arrangement while being in contact with the skin.

The devices 100, 100', 100", 100''' shown in the above examples are only exemplary embodiments. Variations of design and number of components are of course possible according to the desired application and/or if different sizes and costs of the device are considered. In particular, different types of pumps, not limited to peristaltic pumps, and different types of fluidic connectors may be used as far as in the pre-operational arrangement the pump is in a mechanically distressed condition preventing functional operation of the pump and/or the reservoir is fluidically disconnected from the pump, and in the operational arrangement the pump is in a mechanically stressed condition enabling functional operation of the pump and the reservoir is fluidically connected to the pump. Also, the safe-lock mechanism 70,70' is optional or may be of different type than that described herein. Also, instead of ferromagnetic elements 59, 59' the pump 50, 50' may comprise permanent magnets or the device may comprise an internal energy source. Also, the device may comprise a reservoir push element (not shown), e.g. similar to the fluidic connector 32 or the diaphragm 80, 80' but adapted to push on the reservoir in the rearrangement from a first pre-operational arrangement into a second pre-operational or into the operational arrangement such as to push a volume of medicament out of the reservoir thereby achieving priming of the device.

Of course numerous variations of the described embodiments are possible without departing from the scope of the invention. It is also noted that terms like "typically" or "typical" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

The invention claimed is:

1. A medical device for trans-dermal infusion of a medicament, comprising:
    a housing comprising a base and a cover, the housing enclosing:
        a reservoir for holding a medicament,
        a tubing for transporting the medicament from the reservoir to an infusion element, and
        a pump for pumping the medicament through the tubing,
    wherein the medical device, comprising the reservoir, the tubing and the pump, all enclosed within the housing, is pre-assembled in at least one first pre-operational arrangement and is configured to be converted from the said at least one first pre-operational arrangement into a subsequent pre-operational arrangement,
    wherein, in the at least one first pre-operational arrangement, the reservoir is fluidically disconnected from the tubing at an interface between the tubing and the reservoir in order to contain the medicament in the reservoir in a sealed condition,
    wherein, upon being converted from the at least one first pre-operational arrangement into the subsequent pre-operational arrangement, the reservoir becomes fluidically connected to the tubing via an outlet port of the reservoir, thereby allowing the medicament to flow into the tubing, and wherein the medical device is configured to be converted from the subsequent pre-operational arrangement into an operational arrangement, wherein the filling of at least a part of an inner volume of the tubing with the medicament is achieved before the device becomes operational.

2. The medical device according to claim 1 wherein the reservoir is preloaded with medicament.

3. The medical device according to claim 1 wherein in the at least one first pre-operational arrangement the pump is in a mechanically distressed condition preventing functional operation of the pump, and wherein upon conversion from the at least one first pre-operational arrangement into the subsequent pre-operational arrangement or from the subsequent pre-operational arrangement into the operational arrangement the pump becomes mechanically stressed enabling functional operation of the pump.

4. The medical device according to claim 1 wherein the medical device comprises an infusion element or is adapted to be fluidically connected to an infusion element, the infusion element being adapted for trans-dermal infusion of the medicament.

5. The medical device according to claim 4 wherein the infusion element is displaceable such as to penetrate the skin as a result of conversion from the at least one first pre-operational arrangement into the subsequent pre-operational arrangement or from the subsequent pre-operational arrangement into the operational arrangement while the medical device is in contact with the skin.

6. The medical device according to claim 1 wherein in the at least one first pre-operational arrangement the tubing is mechanically distressed and wherein in the operational arrangement the tubing is mechanically stressed.

7. The medical device according to claim 6 wherein the pump is a peristaltic pump adapted to exercise peristaltic pumping when the tubing is mechanically stressed.

8. The medical device according to claim 7 wherein the pump comprises an epicyclic gear system comprising a plurality of planet gears and a central gear.

9. The medical device according to claim 1 wherein the reservoir is fluidically accessible from outside of the device via a filling port so that medicament can be introduced into the reservoir through the port and wherein in the operational arrangement the reservoir is inaccessible from the outside of the device so that medicament is prevented from being introduced into the reservoir.

10. The medical device according to claim 1 wherein the medical device comprises a reservoir push element adapted to push a volume of medicament out of the reservoir, which fills at least a part of an inner volume of the tubing when the device is converted from the at least one first pre-operational arrangement into the subsequent pre-operational arrangement or into the operational arrangement.

11. The medical device according to claim 1 wherein conversion from the pre-operational arrangements to the operational arrangement is irreversible.

12. A kit comprising a plurality of components adapted to be assembled together such as to form a medical device in a pre-operational arrangement according to claim 1.

13. A method of manufacturing a device according to claim 1 comprising assembling the device into at least one pre-operational arrangement and/or manufacturing device components adapted to be assembled into at least one pre-operational arrangement.

* * * * *